United States Patent
Givskov et al.

(10) Patent No.: US 10,258,640 B2
(45) Date of Patent: Apr. 16, 2019

(54) **METHOD OF INHIBITING QUORUM SENSING IN *PSEUDOMONAS AERUGINOSA***

(71) Applicants: Nanyang Technological University, Singapore (SG); National University of Singapore, Singapore (SG)

(72) Inventors: Michael Christian Givskov, Singapore (SG); Shu Sin Chng, Singapore (SG); Liang Yang, Singapore (SG); Zhen Wei Leon Tan, Singapore (SG); Ziyan Hong, Singapore (SG)

(73) Assignees: NANYANG TECHNOLOGICAL UNIVERSITY, Singapore (SG); NATIONAL UNIVERSITY OF SINGAPORE, Singapore (SG)

( * ) Notice: Subject to any disclaimer, the term of this patent is extended or adjusted under 35 U.S.C. 154(b) by 0 days.

(21) Appl. No.: 15/758,666

(22) PCT Filed: Sep. 6, 2016

(86) PCT No.: PCT/SG2016/050436
§ 371 (c)(1),
(2) Date: Mar. 8, 2018

(87) PCT Pub. No.: WO2017/044044
PCT Pub. Date: Mar. 16, 2017

(65) Prior Publication Data
US 2018/0243331 A1    Aug. 30, 2018

(30) Foreign Application Priority Data
Sep. 8, 2015   (SG) .......................... 10201507262 U

(51) Int. Cl.
| | | |
|---|---|---|
| A61K 31/7135 | (2006.01) | |
| A01N 59/26 | (2006.01) | |
| A01N 59/16 | (2006.01) | |
| A61K 33/24 | (2019.01) | |

(52) U.S. Cl.
CPC .......... *A61K 31/7135* (2013.01); *A01N 59/16* (2013.01); *A01N 59/26* (2013.01); *A61K 33/24* (2013.01)

(58) Field of Classification Search
CPC .... A61K 31/7135; A61K 33/24; A01N 59/16; A01N 59/26
USPC ........................................................ 514/24
See application file for complete search history.

(56) References Cited

U.S. PATENT DOCUMENTS

| | | |
|---|---|---|
| 2004/0202639 A1 | 10/2004 | DeGrado et al. |
| 2011/0150961 A1 | 6/2011 | Perry et al. |

FOREIGN PATENT DOCUMENTS

| | | |
|---|---|---|
| WO | 2012/076016 A1 | 6/2012 |
| WO | 2013/181694 A1 | 12/2013 |
| WO | 2014/142748 A1 | 9/2014 |
| WO | 2015/181550 A1 | 12/2015 |
| WO | 2015/181551 A1 | 12/2015 |

OTHER PUBLICATIONS

Cady et al., "Inhibition of Biofilm Formation, Quorum Sensing and Infection in *Pseudomonas aeruginosa* by Natural Products-Inspired Organosulfur Compounds," *PLoS ONE* 7(6):e38492, 2012. (13 pages).
Christensen et al., "Synergistic antibacterial efficacy of early combination treatment with tobramycin and quorum-sensing inhibitors against *Pseudomonas aeruginosa* in an intraperitoneal foreign-body infection mouse model," *J Antimicrob Chemother* 67:1198-1206, 2012.
Givskov, "Bacterial Signaling Systems As Antimicrobial Targets," Oct. 2015, URL=http://microbiology.ku.dk/2015-cmc-symposium/, download date Nov. 17, 2016, 52 pages.
Glišić et al., "Gold complexes as antimicrobial agents: an overview of different biological activities in relation to the oxidation state of the gold ion and the ligand structure," *Dalton Trans* 43:5950-5969, 2014.
Harbut et al., "Auranofin exerts broad-spectrum bactericidal activities by targeting thiol-redox homeostasis," *PNAS* 112(14):4453-4458, 2015.
International Search Report, dated Nov. 29, 2016, for International Application No. PCT/SG2016/050436, 4 pages.
O'Loughlin et al., "A quorum-sensing inhibitor blocks *Pseudomonas aeruginosa* virulence and biofilm formation," *PNAS* 110(44):17981-17986, 2013.
Extended European Search Report, dated Feb. 11, 2019, for European Application No. 16844811.6, 12 pages.

*Primary Examiner* — Kristin A Vajda
(74) *Attorney, Agent, or Firm* — Seed IP Law Group LLP

(57) ABSTRACT

A method of inhibiting quorum sensing in *Pseudomonas aeruginosa* is provided. The method comprises contacting *Pseudomonas aeruginosa* with a gold(I) thiolate complex in an amount effective to inhibit quorum sensing in the *Pseudomonas aeruginosa*. Use of the method for the treatment or prevention of damage or disease associated with quorum sensing and/or biofilm formation in a subject, or for the treatment of biofilm and/or for inhibiting biofilm formation is also provided.

20 Claims, 9 Drawing Sheets

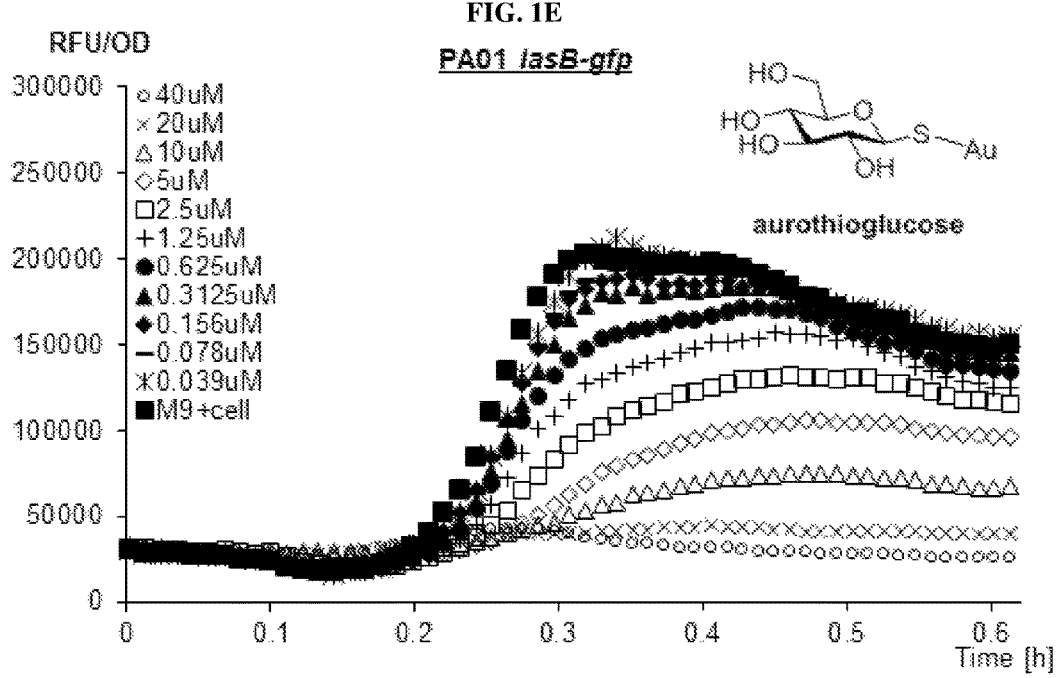
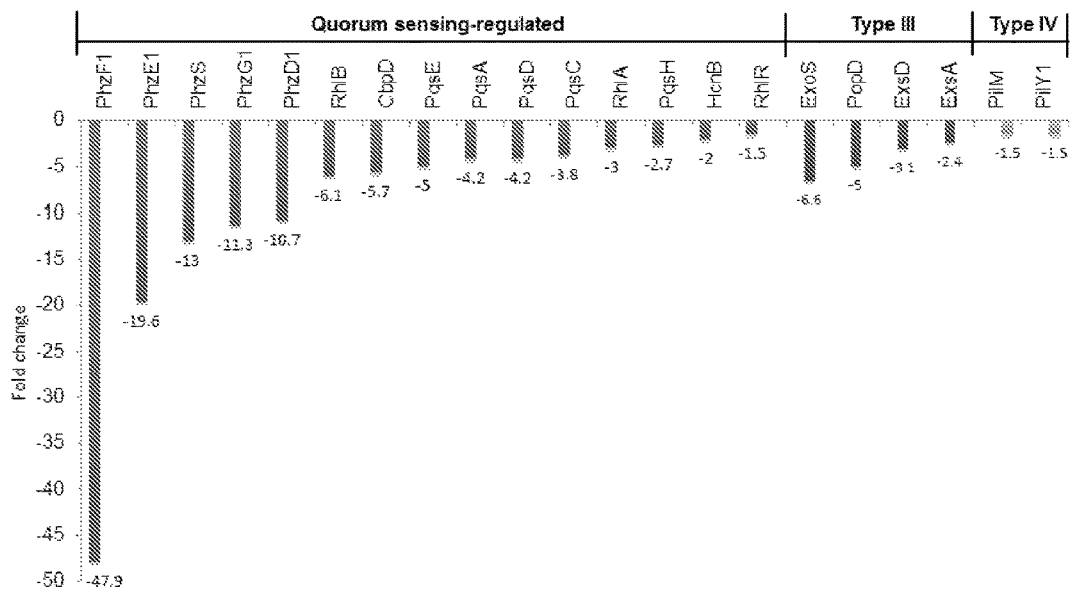

METHOD OF INHIBITING QUORUM SENSING IN *PSEUDOMONAS AERUGINOSA*

CROSS-REFERENCE TO RELATED APPLICATION

This application claims the benefit of priority of Singapore patent application No. 10201507262U filed on 8 Sep. 2015, the content of which is incorporated herein by reference in its entirety for all purposes.

TECHNICAL FIELD

Various embodiments refer to a method of inhibiting quorum sensing in *Pseudomonas aeruginosa*.

BACKGROUND

Microorganisms such as bacteria may communicate via a phenomenon termed quorum sensing (QS), in which they secrete chemical signal molecules termed autoinducers into their surrounding environment. Concentration of these signal molecules may increase locally as a result of increase in cell density, such that upon reaching a threshold level when the cell population is 'quorate', the population activates a coordinated cellular response, such as production of virulence factors and growth as a biofilm community.

Taking *Pseudomonas aeruginosa* (or simply *P. aeruginosa*) as an example, it is a ubiquitous Gram-negative bacterium which is responsible for many opportunistic and nosocomial infections. For example, it is an opportunistic human pathogen that can cause chronic infections in immunocompromised individuals, including cystic fibrosis and intensive-care-unit patients. Notably, chronic infection by *P. aeruginosa* is the leading cause of death of cystic fibrosis patients.

*P. aeruginosa* has three main quorum sensing systems. The first two quorum sensing systems, LasR-LasI and RhlR-RhlI, are based on the LuxR-LuxI homologues of *Vibrio fischeri*, which makes use of acyl homoserine lactone (AHLs) as signal molecules. The AHL synthases are LasI and RhlI, which produce N-(3-oxododecanoyl)-L-homoserine lactone (OdDHL) and N-butanoylhomoserine lactone (BHL), respectively. The receptor for OdDHL is the LasR protein, while the receptor for BHL is the RhlR protein. Together, the las and rhl quorum sensing systems regulate a host of virulence factors such as exoproteases (an example being elastase), siderophores, and toxins.

The third signaling system utilizes another kind of signal molecule, 2-heptyl-3-hydroxy-4-quinolone, that has been termed the *Pseudomonas* quinolone signal (PQS) and is able to affect the expression of Las and Rhl-controlled genes. LasR is an attractive target for quorum sensing inhibition as LasR controls the other quorum sensing circuits (namely Rhl and PQS) within the *P. aeruginosa* hierarchy. The las and rhl systems are at the top and bottom of the hierarchy respectively, while the PQS system intervenes between them.

During infection, the Gram-negative bacterium may reside within multicellular bacterial communities termed biofilms, which are characterized by their extreme tolerance towards conventional antimicrobial agents. *P. aeruginosa* biofilms also have an almost infinite capacity to evade and counter host innate immune responses through secretion of virulence factors, such as a rhamnolipid-based shield.

As quorum sensing controls the expression of multiple virulence factors in different bacteria, blocking or inhibition of quorum sensing would be vital in attenuating the virulence of pathogenic bacteria, and for downplaying biofilm defenses against host attacks, leading to more efficient clearing of the bacterial infection. Further, as quorum sensing inhibitors (for short, QSIs) function as an antimicrobial agent by interrupting bacterial communication, which is a non-essential process, strong selective pressure for the evolution of resistance mechanisms is not exerted, as compared to conventional growth-inhibitory compounds which inhibit growth of the microorganisms.

In view of the above, there exists a need for an improved method of inhibiting quorum sensing in microorganisms such as *Pseudomonas aeruginosa* that addresses or alleviates one or more of the above mentioned problems.

SUMMARY

In a first aspect, a method of inhibiting quorum sensing in *Pseudomonas aeruginosa* is provided. The method comprises contacting *Pseudomonas aeruginosa* with a gold(I) thiolate complex in an amount effective to inhibit quorum sensing in the *Pseudomonas aeruginosa*.

In a second aspect, use of a method according to the first aspect for the treatment or prevention of damage or disease associated with quorum sensing and/or biofilm formation in a subject is provided.

In a third aspect, use of a method according to the first aspect for the treatment of biofilm and/or for inhibiting biofilm formation of a medical device, personal hygiene article, toiletries, cosmetics, disinfectant, cleaning solution, or in a water treatment or distribution system is provided.

BRIEF DESCRIPTION OF THE DRAWINGS

The invention will be better understood with reference to the detailed description when considered in conjunction with the non-limiting examples and the accompanying drawings, in which:

FIG. 1E shows aurothioglucose completely inhibiting the induction of las (PA01 lasB-gfp) quorum-sensing networks in *P. aeruginosa* via a graphical plot of RFU/OD against time at various micromolar concentrations.

FIG. 2 shows down-regulation of quorum sensing-regulated proteins, Type III secretion proteins, and Type IV pilus assembly proteins in auranofin-treated *P. aeruginosa* cultures by proteomic analysis.

DETAILED DESCRIPTION

Figure 1A:
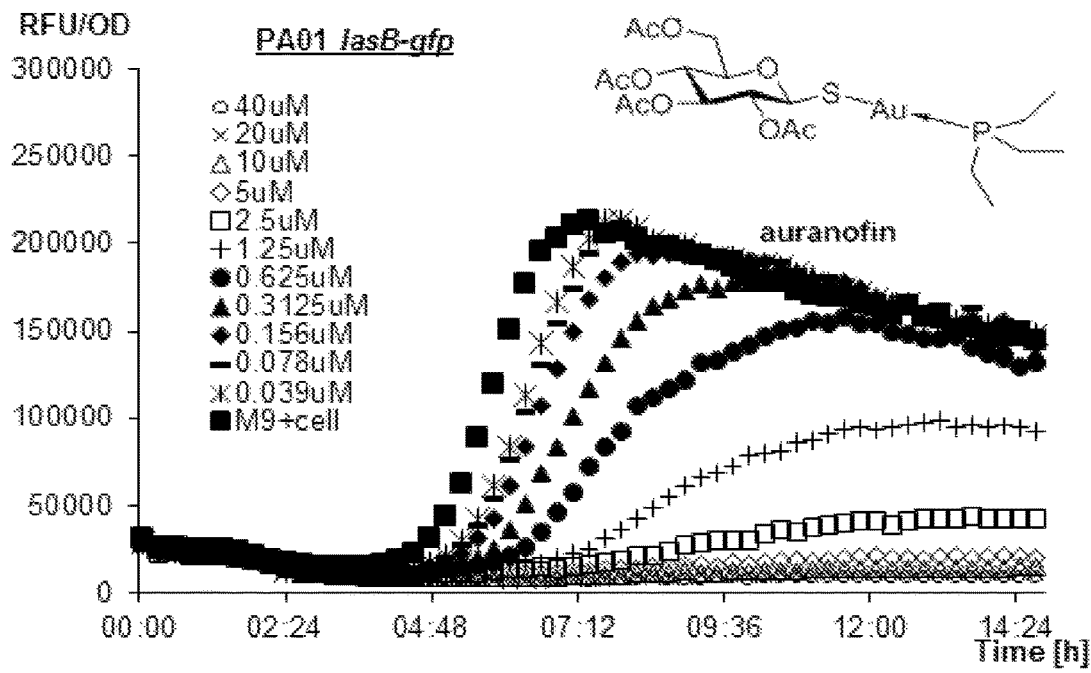
FIG. 1A shows auranofin completely inhibiting the induction of las (PA01 lasB-gfp) quorum-sensing networks in *P. aeruginosa* (PA01) via a graphical plot of relative fluorescence unit/absorbance (RFU/OD) against time at various micromolar concentrations.

Various embodiments refer in a first aspect to a method of inhibiting quorum sensing in *Pseudomonas aeruginosa*.

As used herein, the term "quorum sensing" refers to cell-to-cell or intercellular communication between microorganisms such as bacteria. The quorum sensing system is an attractive anti-bacterial target as a wide spectrum of organisms use quorum sensing to control virulence factor production and other phenotypes such as biofilm formation, coupled with the fact that it is not found in humans and is critical for high level bacterial virulence.

The sensing mechanism is mediated by various diffusible, chemical signal molecules termed as "autoinducers" which are produced by synthase genes of the microorganism. The extracellular concentration of these signal molecules increases as a function of cell density, and is permeable to cell membrane. Upon attaining a threshold concentration of the chemical signals, a quorum sensing cascade is activated to elicit expressions or repressions of multiple genes, including those that are functional for production of autoinducers such as acyl homoserine lactones (AHLs) and their derivatives with different acyl side chains. This organic signaling cascade in turn regulates in a cell-density dependent manner, a myriad of physiological activities unique to the life-cycle of each microorganism such as swarming, cell motility, biofilm formation and growth, conjugation, bioluminescence and/or production of pigments, antibiotics and enzymes.

In *Pseudomonas aeruginosa*, for example, quorum sensing pathways affect the expression of various exoenzymes, biofilm formation and cell-cell spacing. Pathogenic organisms using this signaling system to control virulence could potentially be rendered avirulent by blocking this cell-cell communication system. In contrast to traditional antibiotics, the risk of resistance development is very low, since quorum sensing blocking agents or inhibitors (QSIs) would not kill the organism but disturb signal transduction pathways.

According to embodiments disclosed herein, gold(I) thiolate complexes exemplified by auranofin, sodium aurothiomalate, and aurothioglucose have been shown to inhibit quorum sensing networks in microorganisms, such as *Pseudomonas aeruginosa*. The term "inhibit" is used herein to describe ability of the gold(I) thiolate complex to at least partially block, block, reduce or interfere with communication between cells in the microorganism, thereby inhibiting quorum sensing in the microorganism. The inhibition of quorum sensing networks by gold(I) thiolate complexes such as auranofin may proceed in part via direct inhibition of Vfr, which is a cyclic-AMP-dependent transcription regulator.

*P. aeruginosa* is able to form infectious biofilms on surfaces as diverse as cystic fibrosis lung tissue, contact lenses, and catheter tubes. Since biofilm formation of *P. aeruginosa* has been demonstrated to require an acyl homoserine lactone (AHL) signaling system, inhibition of its quorum sensing system would result in an impaired ability to form biofilms and therefore in an increased susceptability to antibacterial treatment. In experiments demonstrated herein, low micromolar concentrations of auranofin have been shown to prevent induction of all three levels of quorum sensing circuits (las, rhl and pqs) in *P. aeruginosa*, while not affecting growth of *P. aeruginosa*.

With the above in mind, the method according to the first aspect comprises contacting *Pseudomonas aeruginosa* with a gold(I) thiolate complex in an amount effective to inhibit quorum sensing in the *Pseudomonas aeruginosa*

In various embodiments, the gold(I) thiolate complex has Formula (I)

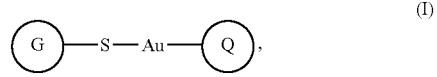

(I)

wherein G is selected from the group consisting of a substituted or unsubstituted $C_1$-$C_{20}$ alkyl, a substituted or unsubstituted $C_1$-$C_{20}$ alkoxy, a substituted or unsubstituted $C_2$-$C_{20}$ alkenyl, a substituted or unsubstituted $C_2$-$C_{20}$ alkynyl, a substituted or unsubstituted $C_3$-$C_{20}$ alicyclic group, a substituted or unsubstituted $C_5$-$C_{15}$ aryl, a substituted or unsubstituted $C_6$-$C_{30}$ alkyl-aryl, a substituted or unsubstituted $C_3$-$C_{20}$ heterocycle, a substituted or unsubstituted $C_4$-$C_{30}$ alkyl-heterocycle, a substituted or unsubstituted $C_5$-$C_{15}$ heteroaryl, and Q is nothing, halogen, or —$PR_3$, wherein each R is independently selected from the group consisting of H, halogen, a substituted or unsubstituted $C_1$-$C_{20}$ alkyl, a substituted or unsubstituted $C_1$-$C_{20}$ alkoxy, a substituted or unsubstituted $C_2$-$C_{20}$ alkenyl, a substituted or unsubstituted $C_2$-$C_{20}$ alkynyl, and a substituted or unsubstituted $C_5$-$C_{15}$ aryl; or a salt thereof.

In present context, the term "aliphatic", alone or in combination, refers to a straight chain (i.e. linear) or branched chain hydrocarbon comprising at least one carbon atom. In certain embodiments, aliphatics are optionally substituted, i.e. substituted or unsubstituted. Aliphatics include alkyls, alkenyls, and alkynyls. Aliphatics include, but are not limited to, methyl, ethyl, propyl, isopropyl, butyl, isobutyl, tert-butyl, pentyl, hexyl, ethenyl, propenyl, butenyl, ethynyl, butynyl, propynyl, and the like.

The term "optionally substituted" or "substituted or unsubstituted" as used herein refers to a group in which none, one, or more than one of the hydrogen atoms have been replaced with one or more groups such as, but are not limited to, alkyl, heteroalkyl, haloalkyl, heterohaloalkyl, cycloalkyl, aryl, arylalkyl, heteroaryl, non-aromatic heterocycle, halogen, cyano, carboxy, hydroxy, nitro, silyl, or amino group.

The term "linear", as used herein, refers to each of the carbon atom backbone chains having no branch point. The term "branched" means a chain of atoms with one or more side chains attached to it. Branching occurs by the replacement of a substituent, e.g. a hydrogen atom, with a covalently bonded substituent or moiety, e.g. an alkyl group.

The term "halogen", as used herein, refers to a member of the halogen family selected from the group consisting of fluorine, chlorine, bromine, and iodine.

In present context, the term "alkyl", alone or in combination, refers to a fully saturated aliphatic hydrocarbon. The alkyl may be linear or branched. In certain embodiments, alkyls are optionally substituted. In certain embodiments, an alkyl comprises 1 to 20 carbon atoms, for example 1 to 10 carbon atoms, wherein (whenever it appears herein in any of the definitions given below) a numerical range, such as "1 to 20" or "$C_1$-$C_{20}$", refers to each integer in the given range, e.g. "$C_1$-$C_{20}$ alkyl" means that an alkyl group comprising only 1 carbon atom, 2 carbon atoms, 3 carbon atoms, 4 carbon atoms, 5 carbon atoms, 6 carbon atoms, 7 carbon atoms, 8 carbon atoms, 9 carbon atoms, 10 carbon atoms, 11 carbon atoms, 12 carbon atoms, 13 carbon atoms, 14 carbon atoms, 15 carbon atoms, 16 carbon atoms, 17 carbon atoms, 18 carbon atoms, 19 carbon atoms, or 20 carbon atoms. Lower alkyl means 1 to 8, preferably 1 to 6, more preferably 1 to 4 carbon atoms.

Examples of the alkyl group include methyl, ethyl, 1-propyl or n-propyl ("n-Pr"), 2-propyl or isopropyl ("i-Pr"), 1-butyl or n-butyl ("n-Bu"), 2-methyl-1-propyl or isobutyl ("i-Bu"), 1-methylpropyl or s-butyl ("s-Bu"), and 1,1-dimethylethyl or t-butyl ("t-Bu"). Other examples of the alkyl group include 1-pentyl, 2-pentyl, 3-pentyl, 2-methyl-2-butyl, 3-methyl-2-butyl, 3-methyl-1-butyl, 2-methyl-1-butyl, 1-hexyl, 2-hexyl, 3-hexyl, 2-methyl-2-pentyl, 3-methyl-2-pentyl, 4-methyl-2-pentyl, 3-methyl-3-pentyl, 2-methyl-3-pentyl, 2,3-dimethyl-2-butyl and 3,3-dimethyl-2-butyl groups.

In present context, the term "alkoxy", alone or in combination, refers to an aliphatic hydrocarbon having an alkyl-O— moiety. The alkoxy may be linear or branched. In certain embodiments, alkoxy groups are optionally substituted. In various embodiments, the alkoxy comprises 1 to 20 carbon atoms, i.e. $C_1$-$C_{20}$ alkoxy. Examples of alkoxy groups include, but are not limited to, methoxy, ethoxy, propoxy, butoxy and the like.

In present context, the term "alkenyl", alone or in combination, refers to an aliphatic hydrocarbon having one or more carbon-carbon double-bonds, such as two or three carbon-carbon double-bonds. The alkenyl may be linear or branched. In certain embodiments, alkenyls are optionally substituted, i.e. substituted or unsubstituted. In certain embodiments, an alkenyl comprises 2 to 20 carbon atoms, such as 2 to 18, or 2 to 12, or 2-6 carbon atoms. "$C_2$-$C_{20}$ alkenyl" means that an alkenyl group comprising only 2 carbon atoms, 3 carbon atoms, 4 carbon atoms, 5 carbon atoms, 6 carbon atoms, 7 carbon atoms, 8 carbon atoms, 9 carbon atoms, 10 carbon atoms, 11 carbon atoms, 12 carbon atoms, 13 carbon atoms, 14 carbon atoms, 15 carbon atoms, 16 carbon atoms, 17 carbon atoms, 18 carbon atoms, 19 carbon atoms, or 20 carbon atoms. Lower alkenyl means 2 to 8, 2 to 6 or 2 to 4 carbon atoms. Examples of alkenyls include, but are not limited to, ethenyl, propenyl, butenyl, 1,4-butadienyl, pentenyl, hexenyl, 4-methylhex-1-enyl, 4-ethyl-2-methylhex-1-enyl and the like.

In present context, the term "alkynyl", alone or in combination, refers to an aliphatic hydrocarbon having one or more carbon-carbon triple-bonds, such as two or three carbon-carbon triple-bonds. The alkynyl may be linear or branched. In certain embodiments, alkynyls are optionally substituted, i.e. substituted or unsubstituted. In certain embodiments, an alkynyl comprises 2 to 20 carbon atoms, such as 2 to 18, or 2 to 12, or 2 to 6 carbon atoms. "$C_2$-$C_{20}$ alkynyl" means that an alkynyl group comprising only 2 carbon atoms, 3 carbon atoms, 4 carbon atoms, 5 carbon atoms, 6 carbon atoms, 7 carbon atoms, 8 carbon atoms, 9 carbon atoms, 10 carbon atoms, 11 carbon atoms, 12 carbon atoms, 13 carbon atoms, 14 carbon atoms, 15 carbon atoms, 16 carbon atoms, 17 carbon atoms, 18 carbon atoms, 19 carbon atoms, or 20 carbon atoms. Lower alkynyl means 2 to 8, 2 to 6 or 2 to 4 carbon atoms. Examples of alkynyls include, but are not limited to, ethynyl, propynyl, butynyl, and the like.

In present context, the term "non-aromatic ring" refers to a group comprising a covalently closed ring that is not aromatic. The term "alicyclic" refers to a group comprising a non-aromatic ring wherein each of the atoms forming the ring is a carbon atom, and may be further classified into monocyclic and polycyclic (e.g., bicyclic and tricyclic) groups. Alicyclic groups may be formed of 3 to 20, or 3 to 12, or 3 to 8, or 3 to 6 carbon atoms, such as three, four, five, six, seven, eight, nine, or more than nine carbon atoms. In certain embodiments, alicyclics are optionally substituted, i.e. substituted or unsubstituted. In certain embodiments, an alicyclic comprises one or more unsaturated bonds, such as one or more carbon-carbon double-bonds. Alicyclics include cycloalkyls and cycloalkenyls. Examples of alicyclics include, but are not limited to, cyclopropane, cyclobutane, cyclopentane, cyclopentene, cyclopentadiene, cyclohexane, cyclohexene, 1,3-cyclohexadiene, 1,4-cyclohexadiene, cycloheptane, and cycloheptene.

In present context, the term "aryl" refers to an aromatic ring wherein each of the atoms forming the ring is a carbon atom. Aryl rings may be formed by five, six, seven, eight, nine, or more than nine carbon atoms. Aryl groups may be optionally substituted. For example, an aryl group may be 5- and 6-membered carbocyclic aromatic rings, such as, phenyl; bicyclic ring systems such as 7-12 membered bicyclic ring systems wherein at least one ring is carbocyclic and aromatic, selected, for example, from naphthalene, indane, and 1,2,3,4-tetrahydroquinoline; and tricyclic ring systems such as 10-15 membered tricyclic ring systems wherein at least one ring is carbocyclic and aromatic, for example, fluorene.

The term "alkyl aryl", as used herein, generally refers to a chemical substituent containing an alkyl group coupled to an aryl group or a substituted aryl group. The terms "aralkyl" and "aryl alkyl," as used alone or in combination herein, are species of alkyl as defined herein, and particularly refer to an alkyl group as defined above in which one hydrogen atom is replaced by an aryl group as defined above.

The terms "heterocyclic" or "heterocycle" or "heterocyclyl", as interchangeably used herein, refer to a ring selected from 4- to 12-membered monocyclic, bicyclic and tricyclic, saturated and partially unsaturated rings comprising at least one carbon atoms in addition to 1, 2, 3 or 4 heteroatoms, selected from oxygen, sulfur, and nitrogen. "Heterocycle" also refers to a 5- to 7-membered heterocyclic ring comprising at least one heteroatom selected from N, O, and S fused with 5-, 6-, and/or 7-membered cycloalkyl, carbocyclic aromatic or heteroaromatic ring, provided that the point of attachment is at the heterocyclic ring when the heterocyclic ring is fused with a carbocyclic aromatic or a heteroaromatic ring, and that the point of attachment can be at the cycloalkyl or heterocyclic ring when the heterocyclic ring is fused with cycloalkyl.

"Heterocycle" also refers to an aliphatic spirocyclic ring comprising at least one heteroatom selected from N, O, and S, provided that the point of attachment is at the heterocyclic ring. The rings may be saturated or have at least one double bond (i.e. partially unsaturated). The heterocycle may be substituted with oxo. The point of the attachment may be carbon or heteroatom in the heterocyclic ring. A heterocyle is not a heteroaryl as defined herein. Examples of the heterocycle include, but not limited to, (as numbered from the linkage position assigned priority 1) 1-pyrrolidinyl, 2-pyrrolidinyl, 2,4-imidazolidinyl, 2,3-pyrazolidinyl, 1-piperidinyl, 2-piperidinyl, 3-piperidinyl, 4-piperidinyl, 2,5-piperazinyl, pyranyl, 2-morpholinyl, 3-mo holinyl, oxiranyl, aziridinyl, fhiiranyl, azetidinyl, oxetanyl, thietanyl, 1,2-dithietanyl, 1,3-difhietanyl, dihydropyridinyl, tetrahydropyridinyl, thiomorpholinyl, thioxanyl, piperazinyl, homopiperazinyl, homopiperidinyl, azepanyl, oxepanyl, thiepanyl, 1,4-oxathianyl, 1,4-dioxepanyl, 1,4-oxafhiepanyl, 1,4-oxaazepanyl, 1,4-difhiepanyl, 1,4-fhiazepanyl and 1,4-diazepane 1,4-dithianyl, 1,4-azathianyl, oxazepinyl, diazepinyl, thiazepinyl, dihydrofhienyl, dihydropyranyl, dihydrofuranyl, tetrahydrofuranyl, tetrahydrothienyl, tetrahydropyranyl, tetrahydrothiopyranyl, 1-pyrrolinyl, 2-pyrrolinyl, 3-pyrrolinyl, indolinyl, 2H-pyranyl, 4H-pyranyl, 1,4-dioxanyl, 1,3-dioxolanyl, pyrazolinyl, pyrazolidinyl, dithianyl, difhiolanyl, pyrazolidinylimidazolinyl, pyrimidinonyl, 1,1-dioxo-thiomo holinyl, 3-azabicyco[3.1.0]hexanyl, 3-azabicyclo[4.1.0]heptanyl and azabicyclo[2.2.2]hexanyl.

The term "alkyl heterocycle", as used herein, generally refers to a chemical substituent containing an alkyl group coupled to a heterocycle or a substituted heterocycle.

In present context, the term "heteroaryl" refers to an aromatic heterocycle. Heteroaryl rings may be formed by five, six, seven, eight, nine, or more than nine atoms. Heteroaryls may be optionally substituted. Examples of heteroaryl groups include, but are not limited to, aromatic $C_5$-$C_{15}$ heterocyclic groups comprising one oxygen or sulfur atom or up to four nitrogen atoms, or a combination of one oxygen or sulfur atom and up to two nitrogen atoms, and their substituted as well as benzo- and pyrido-fused derivatives, for example, connected via one of the ring-forming carbon atoms.

In various embodiments, G is a substituted or unsubstituted $C_1$-$C_{20}$ alkyl, a substituted or unsubstituted $C_3$-$C_{20}$ heterocycle, or a substituted or unsubstituted $C_4$-$C_{30}$ alkyl-heterocycle.

In some embodiments, G is —C($R^a$)($R^b$)($R^c$), wherein $R^a$, $R^b$, and $R^c$ are independently selected from the group consisting of H, a substituted or unsubstituted $C_1$-$C_{20}$ alkyl, and salts thereof; or

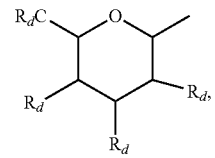

wherein each $R^d$ is independently —OOR' or —OH, wherein R' is a substituted or unsubstituted $C_1$-$C_{20}$ alkyl.

In specific embodiments, G is selected from the group consisting of —CH(COO⁻Na⁺)(CH$_2$COOH),

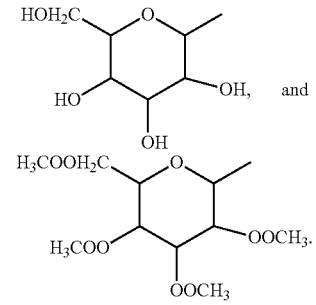

In various embodiments, Q is nothing, —Cl, or —P($R^e$)$_3$, wherein each $R^e$ is independently a substituted or unsubstituted $C_1$-$C_{20}$ alkyl.

In specific embodiments, Q is nothing or —P(CH$_2$CH$_3$)$_3$.

Accordingly, in various embodiments, the gold(I) thiolate complex may be selected from the group consisting of

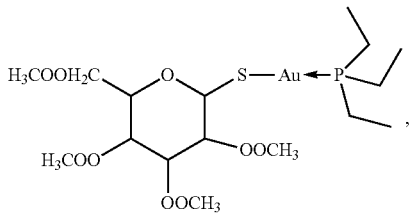

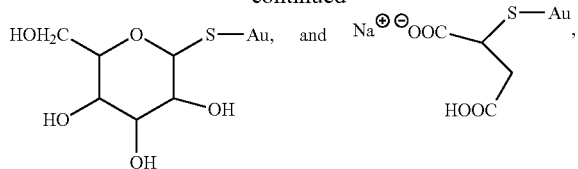

wherein the structures denote respectively, auranofin, aurothioglucose and sodium aurothiomalate.

In some embodiments, the gold(I) thiolate complex is auranofin. Auranofin is an FDA-approved drug and comprises a gold(I) ion coordinated by one thiolate and one phosphine ligand in a linear fashion. Due to its anti-inflammatory activities, it may be used for the treatment of rheumatoid arthritis, and has also been investigated for treatment of cancer and parasitic infections such as malaria and amoebiasis, where it is postulated to work via inhibiting thioredoxin reductases and thioredoxin glutathione reductases, which are enzymes important for maintaining redox balance.

Apart from the above-mentioned, gold(I) thiolate complexes such as aurothiomalate, and/or disodium aurothiomalate having formula $AuSCH(CO_2Na)CH_2CO_2Na$ may also be used.

As mentioned above, gold(I) thiolate complexes, such as auranofin, sodium aurothiomalate, and aurothioglucose have been shown to inhibit quorum sensing in *Pseudomonas aeruginosa*, which is a Gram-negative bacteria. Inhibiting the quorum sensing in *Pseudomonas aeruginosa* may comprise inhibiting a cyclic-AMP-dependent transcription regulator Vfr, which also controls Type III secretion and Type IV pilus assembly. Type IV pilus is also essential for biofilm formation and maturation, thus auranofin targets multiple processes that are important for *P. aeruginosa* virulence and biofilm formation.

The terms "microorganism" and "microbe" are used interchangeably herein, and refer to an organism that is unicellular or lives in a colony of cellular organisms such as bacteria, fungi, protest, or archea. The method of inhibiting quorum sensing disclosed herein is used in *Pseudomonas aeruginosa*, which is a type of Gram-negative quorum sensing bacteria. Other examples of Gram-negative quorum sensing bacteria include: *Aeromonas hydrophila, A. salmonicida, Agrobacterium tumefaciens, Burkholderia cepacia, Chromobacterium violaceum, Enterobacter agglomeran, Erwinia carotovora, E. chrysanthemi, Escherichia coli, Nitrosomas europaea, Obesumbacterium proteus, Pantoea stewartii, Pseudomonas aureofaciens, P. syringae, Ralstonia solanacearum, Rhisobium etli, R. leguminosarum, Rhodobacter sphaeroides, Serratia liguefaciens, S. marcescens, Vibrio anguillarum, V. fischeri, V. cholerae, Xenorhabdus nematophilus, Yersinia enterocolitica, Y. pestis, Y. pseudotuberculosis, Y. medievalis*, and *Y. ruckeri*.

The *Pseudomonas aeruginosa* may be contacted with the gold(I) thiolate complex ex vivo or in vivo.

In various embodiments, the *Pseudomonas aeruginosa* is contacted with the gold(I) thiolate complex ex vivo. The contacting may comprise administering the gold(I) thiolate complex to a surface, such as that of a medical device or a personal hygiene article, in an amount effective to inhibit biofilm formation associated with quorum sensing of the *Pseudomonas aeruginosa* on the surface.

The term "biofilm" as used herein refers to (dense) extracellular polymeric matrices in which the microorganisms embed themselves, thereby resulting in cell aggregations comprising either a single type of microorganism or a mixture of more than one microorganism, then referred to as "mixed biofilms". Biofilms allow the microorganisms to create a microenvironment containing excreted enzymes and other factors on a host surface, such that the microorganisms are able to evade host immune responses including antibodies and cellular immune responses. Biofilms may be extremely resistant to removal and disinfection, and may, for example, be inherent in dental plaques, and may also be present in a wide variety of different fields such as environmental, industrial and medical applications.

The gold(I) thiolate complex may be administered in an amount effective to inhibit biofilm formation associated with quorum sensing of the *Pseudomonas aeruginosa* on the surface. By the term "amount effective to inhibit biofilm formation", it meant a sufficient amount of the compound to provide the desired effect of at least partially blocking, blocking, reducing or interfering with communication between *Pseudomonas aeruginosa* cells, which in turn inhibits forming of a biofilm. Different amounts may be suitable depending, for example, on the gold(I) thiolate complex used.

In various embodiments, the *Pseudomonas aeruginosa* is contacted with the gold(I) thiolate complex in vivo. The contacting may comprise administering the gold(I) thiolate complex to a subject. The term "subject" as used herein refers to a plant or an animal, preferably a mammal, and more preferably a human. The methods disclosed herein are applicable to both human therapy and veterinary applications.

The subject may be afflicted with a disorder associated with quorum sensing and/or biofilm formation, and the gold(I) thiolate complex is administered in an amount effective to treat the disorder.

As used herein, the terms "disorder" and "disease" are used interchangeably and refer to a condition in which there is a disturbance of normal functioning of the body or mind, which may cause discomfort, dysfunction, or distress to the affected subject. Sometimes, the terms are used broadly to also include injuries, disabilities, syndromes, symptoms, deviant behaviors, and atypical variations of structure and function.

Examples of disorder or disease associated with quorum sensing and/or biofilm formation may include, but are not limited to, cystic fibrosis, dental caries, periodonitis, otitis media, muscular skeletal infections, necrotizing fasciitis, biliary tract infection, osteomyelitis, bacterial prostatitis, endocarditis, native valve endocarditis, cystic fibrosis pneumonia, meloidosis, or skin lesions associated with bullous impetigo, atopic dermatitis and pemphigus foliaceus, a nosocomial infection such as pneumonia, or an infection associated with sutures, exit sites, arteriovenous sites, scleral buckles, contact lenses, urinary catheter cystitis, peritoneal dialysis (CAPD) peritonitis, IUDs, endotracheal tubes, Hickman catheters, central venous catheters, mechanical heart valves, vascular grafts, biliary stent blockage, or orthopedic devices.

In various embodiments, the disorder or disease is one that is triggered by *Pseudomonas aeruginosa*. Examples of such disorder or disease include, but are not limited to, endocarditis, respiratory and pulmonary infections (preferably in immunocompromized and cystic fibrosis patients), bacteremia, central nervous system infections, ear infections including external otitis, eye infections, bone and joint infections, urinary tract infections, gastrointestinal infections and skin and soft tissue infections including wound infections, pyoderma and dermatitis.

The gold(I) thiolate complex is administered in an amount effective to treat the disorder. By the terms "amount effective to treat the disorder", "effective amount" and "therapeutically effective amount", it is meant a non-toxic but sufficient amount of the gold(I) thiolate complex to provide the desired effect. The terms "treat", "treating" and "treatment", as used herein, refer to reduction in severity and/or frequency of symptoms, elimination of symptoms and/or underlying cause, prevention of the occurrence of symptoms and/or their underlying cause, and improvement or remediation of damage. This may be carried out by inhibiting quorum sensing cascade in *Pseudomonas aeruginosa* so as to render the pathogen avirulent.

The gold(I) thiolate complex may be administered orally, for example, in the form of pills, tablets, coated tablets, sugar coated tablets, lozenges, hard and soft gelatin capsules, solutions, syrups, emulsions or suspensions or as aerosol mixtures. Administration, however, may also be carried out rectally, for example, in the form of suppositories, or parenterally, for example, in the form of injections or infusions, or percutaneously, for example, in the form of ointments, creams or tinctures.

In various embodiments, the gold(I) thiolate complex is present in a composition comprising a pharmaceutically-acceptable additive, adjuvant, and/or excipient. For example, the gold(I) thiolate complex may be present in a composition containing pharmaceutically-acceptable additives or adjuvants used in galenic formulations, such as fillers, extenders, disintegrants, binders, glidants, wetting agents, stabilizers, emulsifiers, preservatives, sweetening agents, colorants, flavorings or aromatizers, buffer substances, and furthermore solvents or solubilizers or agents for achieving a depot effect, as well as salts for modifying the osmotic pressure, coating agents or antioxidants.

In some embodiments, the gold(I) thiolate complex is present in a composition comprising a pharmaceutically-acceptable excipient. In the present context, a "pharmaceutically acceptable excipient" refers to an inert substance which is added to further facilitate administration of a compound. Examples, without limitation, of excipients include calcium carbonate, calcium phosphate, various sugars and types of starch, cellulose derivatives, gelatine, vegetable oils and polyethylene glycols.

Different excipients may be used. To prepare pills, tablets, coated tablets and hard gelatin capsules, for example, lactose, corn starch or derivatives thereof, talc, stearic acid or its salts may be used. Excipients for soft gelatin capsules and suppositories may, for example, include fats, waxes, semi-solid and liquid polyols, natural or hardened oils. Suitable excipients for the production of solutions and syrups may, for example, include water, alcohol, sucrose, invert sugar, glucose, and/or polyols. Suitable excipients for the production of injection solutions may, for example, include water, alcohol, glycerol, polyols and/or vegetable oils.

Regardless of whether the *Pseudomonas aeruginosa* is contacted with the gold(I) thiolate complex ex vivo or in vivo, the gold(I) thiolate complex may be present in a composition comprising an antibiotic.

The term "antibiotic" as used herein refers to a compound which possesses antibacterial, antifungal, antiviral, and/or antiparasitic activity, where examples include, but are not limited to, cefazolin, cephradine, cefaclor, cephapirin, ceftizoxime, cefoperazone, cefotetan, cefutoxime, cefotaxime, cefadroxil, ceftazidime, cephalexin, cephalothin, cefamandole, cefoxitin, cefonicid, ceforanide, ceftriaxone, cefadroxil, cephradine, cefuroxime, ampicillin, amoxicillin, cyclacillin, ampicillin, penicillin G, penicillin V potassium, piperacillin, oxacillin, bacampicillin, cloxacillin, ticarcillin, azlocillin, carbenicillin, methicillin, nafcillin, erythromycin, tetracycline, doxycycline, minocycline, aztreonam, chloramphenicol, ciprofloxacin hydrochloride, clindamycin, metronidazole, gentamicin, lincomycin, tobramycin, vancomycin, polymyxin B sulfate, colistimethate, colistin, azithromycin, augmentin, sulfamethoxazole, trimethoprim, and derivatives thereof.

In various embodiments, the antibiotic is at least one of colistin or tobramycin.

Advantageously, it has been surprisingly found by the inventors that use of a gold(I) complex such as auranofin in conjunction with an antibiotic produces a synergistic effect in disrupting morphology of biofilm, and killing of the biofilm.

Various embodiments refer in a second aspect to use of a method according to the first aspect for the treatment or prevention of damage or disease associated with quorum sensing and/or biofilm formation in a subject.

Examples of disease associated with quorum sensing and/or biofilm formation in a subject have already been mentioned above. In particular, the method of inhibiting quorum sensing in *Pseudomonas aeruginosa* according to embodiments disclosed herein are useful for the treatment of a variety of human, animal and plant diseases, where bacterial pathogens of *Pseudomonas aeruginosa* regulate the expression of virulence genes and other phenotypes, for example biofilm formation, through an AHL-based quorum sensing system.

In the context of a treatment or prevention of a bacterial damage or disease, a "therapeutically effective amount" or "prophylactically effective amount" of a compound refers to an amount of active agent that is capable of treating, preventing or at least slowing down (lessening) bacterial damage or disease in a subject. Dosages and administration method may be determined by one of ordinary skill in the art of clinical pharmacology or pharmacokinetics. An effective amount of the compound to be employed therapeutically may depend, for example, upon the therapeutic objectives, the route of administration, and the condition of the mammalian subject. Accordingly, the therapist may titer the dosage and modify the route of administration as required to obtain the optimal therapeutic effect.

Various embodiments refer in a further aspect to use of a method according to the first aspect for the treatment of biofilm or for inhibiting biofilm formation of a medical device, personal hygiene article, toiletries, cosmetics, disinfectant, cleaning solution, or in a water treatment or distribution system.

The gold(I) thiolate complex may be used for various kinds of surfaces in private and public areas, where it is beneficial to inhibit quorum sensing systems of Gram-negative *Pseudomonas aeruginosa* bacteria in order to prevent and/or treat colonization and biofilm formation. For example, the gold(I) thiolate complex may be applied to a surface as a solution of the compound, alone or together with other materials such as conventional surfactants, preferably sodium dodecyl sulfate, or detergents, biocides, fungicides, antibiotics, pH regulators, perfumes, dyes or colorants.

In various embodiments, the method of the first aspect may be applied to windows, floors, clothes, kitchen and bathroom surfaces and other surfaces in the area of food preparation and personal hygiene, or in personal hygiene articles, toiletries and cosmetics such as dentifrices, mouth-washes, soaps, shampoos, shower gels, ointments, creams, lotions, deodorants and disinfectants and storage solutions for contact lenses.

The method of the first aspect may also be used to inhibit and/or prevent medical device-associated bacterial infections by inhibiting and/or preventing biofilm formation on a surface of the medical device. The medical device may be surgical instruments, or blood bag systems; more preferably either permanently implanted devices such as artificial heart valve, prostethic joint, voice prosthesis, stent, shunt or not permanently implanted devices such as endotracheal or gastrointestinal tube, pacemaker, surgical pin or indwelling catheter.

The indwelling catheters may be urinary catheters, vascular catheters, peritoneal dialysis catheter, central venous catheters and needleless connectors. The catheter materials may be polyvinylchloride, polyethylene, latex, Teflon, polyurethane and silicone or similar polymeric materials.

The method of the first aspect may also be used to prevent or treat bacterial biofilms in industrial settings such as ship hulls, paper manufacturing, oil recovery and food processing. The method may also be used to prevent or treat bacterial biofilms in water processing plants or drinking water distribution systems where the colonized surface may be the interior of an aqueous liquid system such as water pipes, water injection jets, heat exchangers and cooling towers.

The invention has been described broadly and generically herein. Each of the narrower species and subgeneric groupings falling within the generic disclosure also form part of the invention. This includes the generic description of the invention with a proviso or negative limitation removing any subject matter from the genus, regardless of whether or not the excised material is specifically recited herein.

Other embodiments are within the following claims and non-limiting examples. In addition, where features or aspects of the invention are described in terms of Markush groups, those skilled in the art will recognize that the invention is also thereby described in terms of any individual member or subgroup of members of the Markush group.

EXPERIMENTAL SECTION

Example 1: Inhibition of Quorum Sensing by Auranofin

Figure 1B:
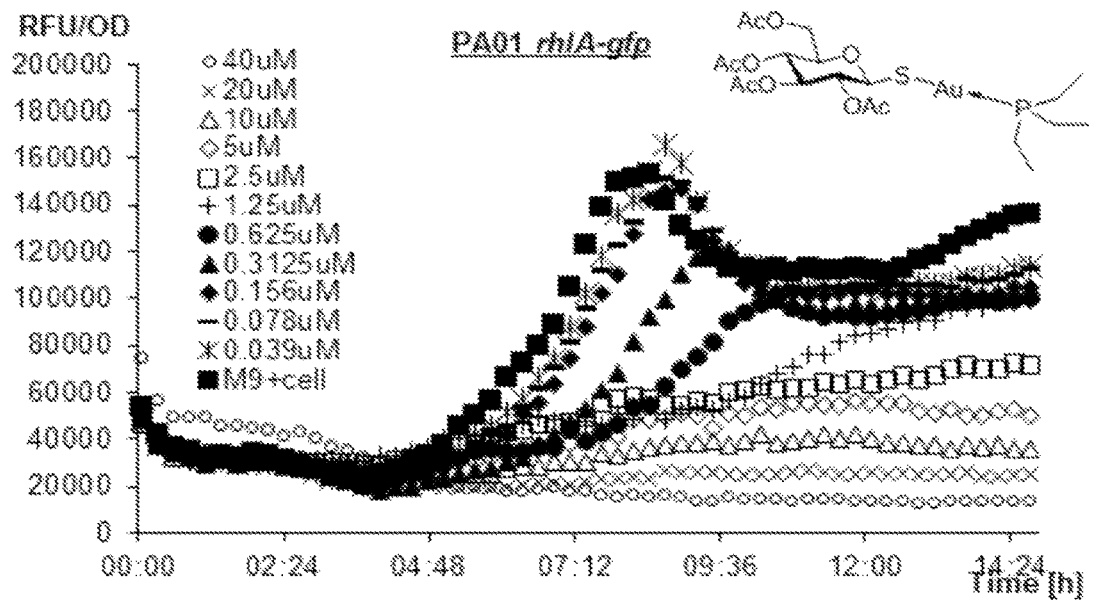
FIG. 1B shows auranofin completely inhibiting the induction of rhl (PA01 rhlA-gfp) quorum-sensing networks in *P. aeruginosa* via a graphical plot of RFU/OD against time at various micromolar concentrations.
Figure 1C:
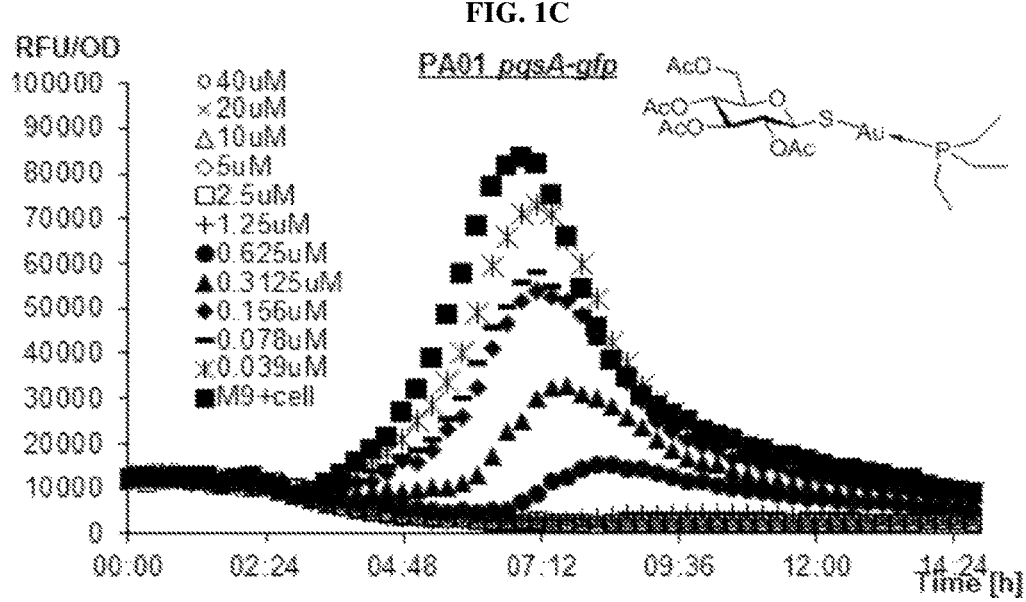
FIG. 1C shows auranofin completely inhibiting the induction of pqs (PA01 pqsA-gfp) quorum-sensing networks in *P. aeruginosa* via a graphical plot of RFU/OD against time at various micromolar concentrations.

The inhibition of quorum sensing has been observed by the inventors during a chemical screen set up to look for small-molecule inhibitors of quorum sensing in *P. aeruginosa*. The assay used is a cell-based fluorescence assay (PA01 lasB-gfp) in which the expression of GFP is controlled by a las-regulated promoter. Inhibition of induction of the las quorum-sensing system by a small molecule is marked by the reduction in GFP signal relative to an untreated sample. Commercially-available chemical libraries (from Enzo Life Sciences: http://www.enzolifesciences.com/welcome/compound-libraries/) were screened and one of the compounds, auranofin, was observed to inhibit the above reporter assay (FIG. 1A). Auranofin also inhibited the induction of two other quorum sensing assays (PA01 rhlA-gfp and pqsA-gfp), which relate to the rhl and pqs systems, respectively (FIGS. 1B and 1C).

Figure 1D:
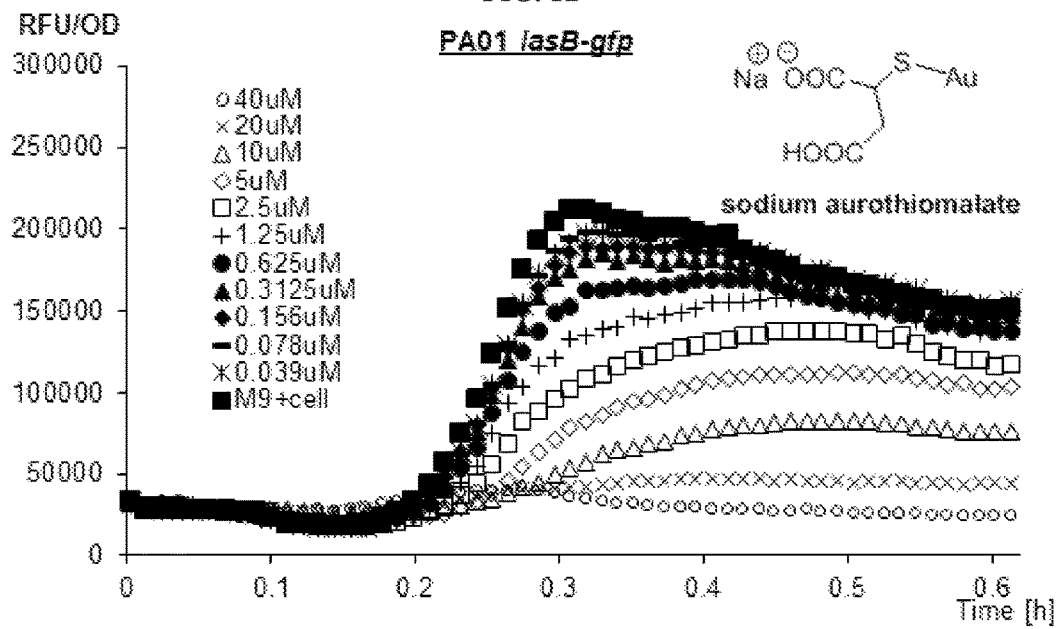
FIG. 1D shows sodium aurothiomalate completely inhibiting the induction of las (PA01 lasB-gfp) quorum-sensing networks in *P. aeruginosa* via a graphical plot of RFU/OD against time at various micromolar concentrations.

Two other gold(I)-containing rheumatoid arthritis drugs also demonstrated inhibition of induction of the lasB-gfp assay, suggesting that this effect may be general to all gold(I)-containing compounds (FIGS. 1D and 1E).

Example 2a: Reduction of Cellular or Protein Expression Via Auranofin

Analysis of *P. aeruginosa* proteome in the presence or absence of auranofin showed that auranofin down-regulated cellular levels of various proteins whose expression are known to be controlled by quorum sensing in *P. aeruginosa* (FIG. 2). This validated the reporter assays as demonstrated above in example 1.

Figure 3:
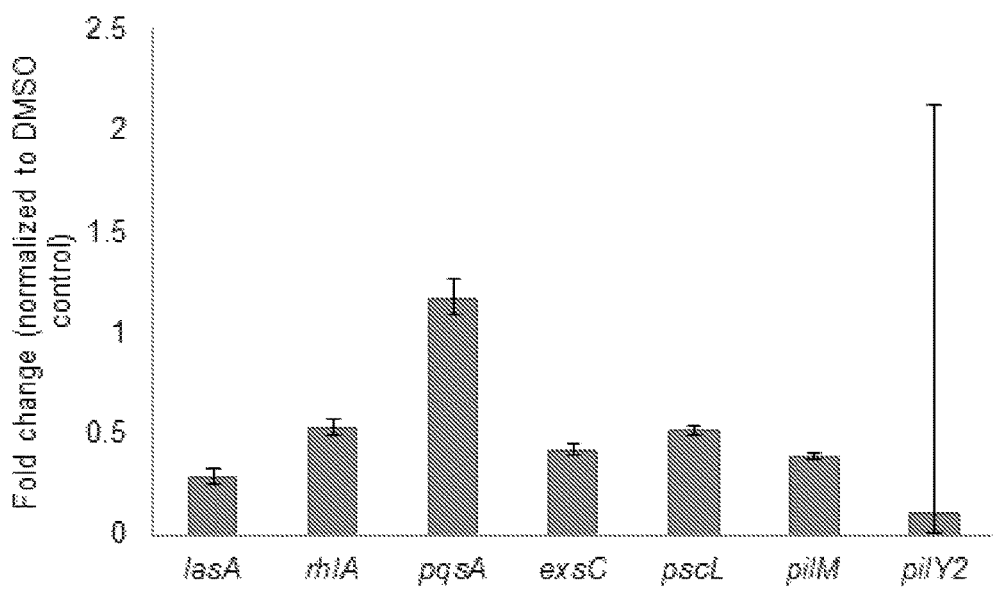
FIG. 3 shows the RNA levels (as determined by quantitative RT-PCR) of quorum-sensing regulated genes (lasA, rhlA and pqsA), Type III secretion genes (exsC and pscL), and Type IV pilus assembly genes (pilM and pilY), that are generally down-regulated upon auranofin treatment.

It was also observed that treatment with auranofin resulted in the down-regulation of proteins involved in Type III secretion and formation of the Type IV pilus (FIG. 2). Meanwhile, quantitative RT-PCR further supported these results (FIG. 3).

Figure 4A:
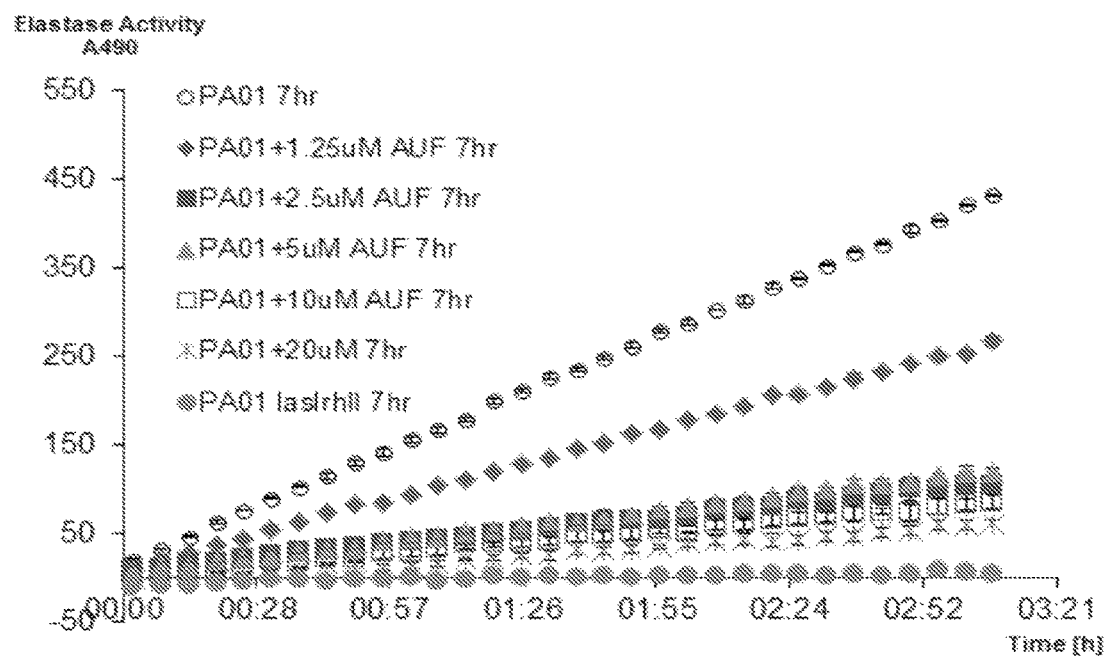
FIG. 4A shows the levels of the activity of virulence factor, elastase (LasB), in culture supernatants after 7 hours of auranofin treatment at various micromolar concentrations. LasB levels were measured using a commercial elastase activity kit.
Figure 4B:
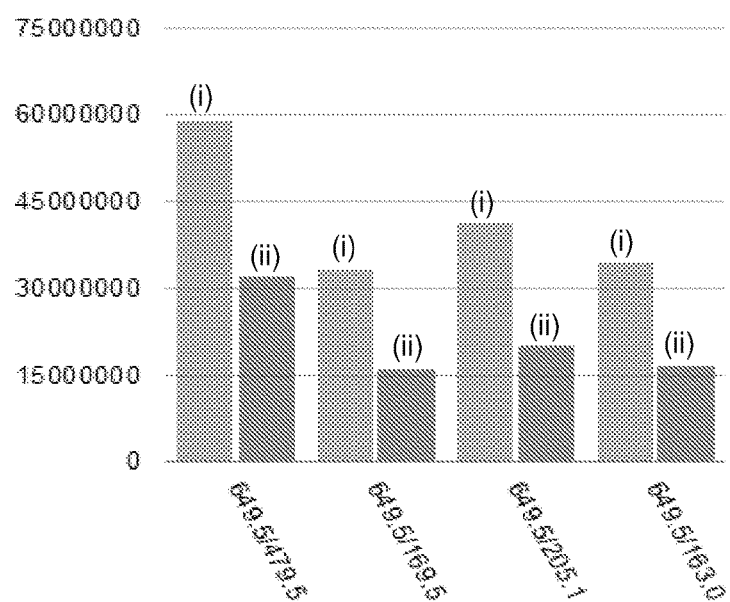
FIG. 4B shows the levels of virulence factor, rhamnolipids, in culture supernatants after 7 hours of auranofin treatment at various micromolar concentrations. Rhamnolipid levels were determined using multiple reaction monitoring (MRM) mass spectrometry.
Figure 4C:
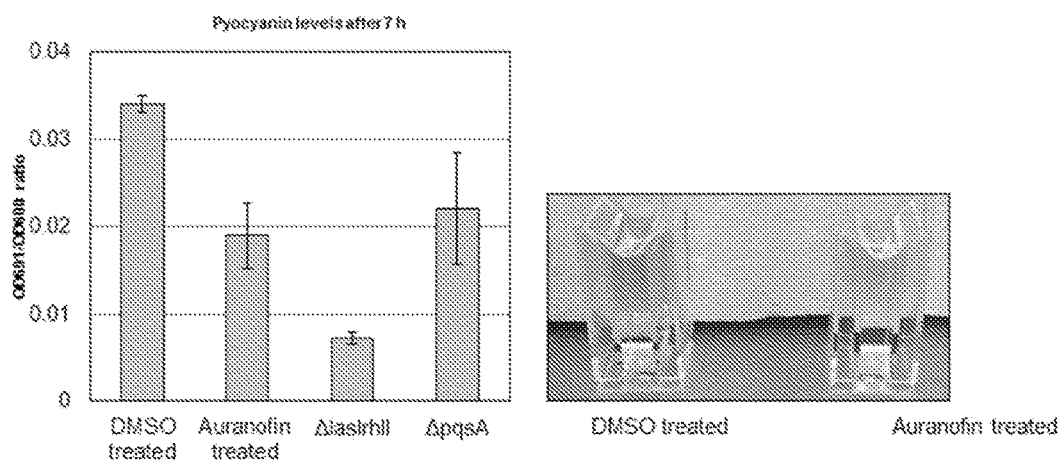
FIG. 4C shows the levels of virulence factor, pyocyanin, in culture supernatants after 7 hours of auranofin treatment at various micromolar concentrations. Pyocyanin levels were determined via absorbance at 691 nm.

Levels of quorum sensing-regulated virulence factors (LasB and rhamnolipids and pyocyanin) were further measured and it was found that these were indeed reduced (FIG. 4A and FIG. 4B and FIG. 4C).

Example 2b: Motility Assays Using Auranofin

Figure 5A:
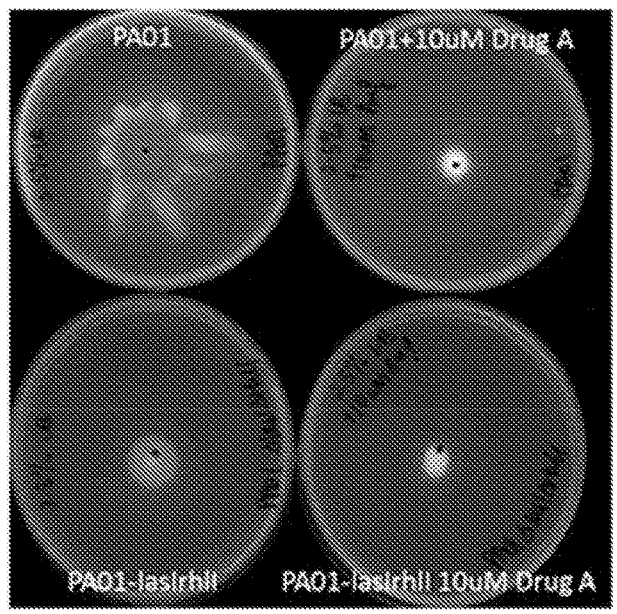
FIG. 5A illustrates the inhibition of swarming motility in *P. aeruginosa* by auranofin (drug A), which requires Type IV pili (top-left dish shows a control assay of PA01, top-right dish shows a PA01 assay with 10 μM drug A, bottom-left dish shows an assay of PA01-lasIrhlI and bottom-right dish shows an assay of PA01-lasIrhlI with 10 μM drug A).
Figure 5B:
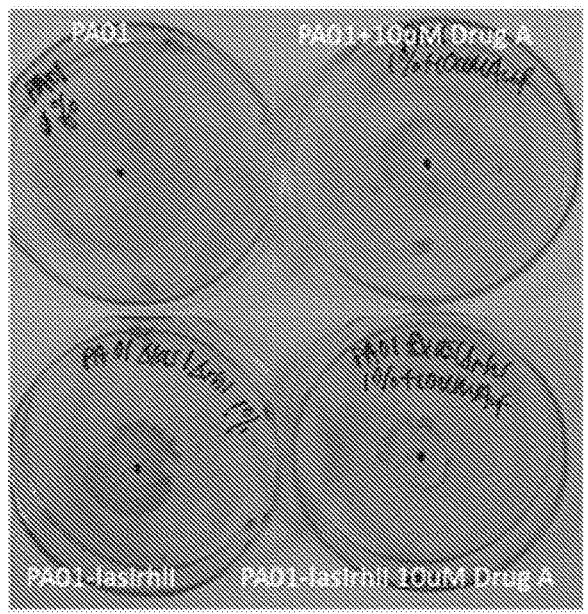
FIG. 5B illustrates the inhibition of twitching motility in *P. aeruginosa* by auranofin (drug A), as mediated by Type IV pili (top-left dish shows a control assay of PA01, top-right dish shows a PA01 assay with 10 μM drug A, bottom-left dish shows an assay of PA01-lasIrhlI and bottom-right dish shows an assay of PA01-lasIrhlI with 10 μM drug A).
Figure 5C:
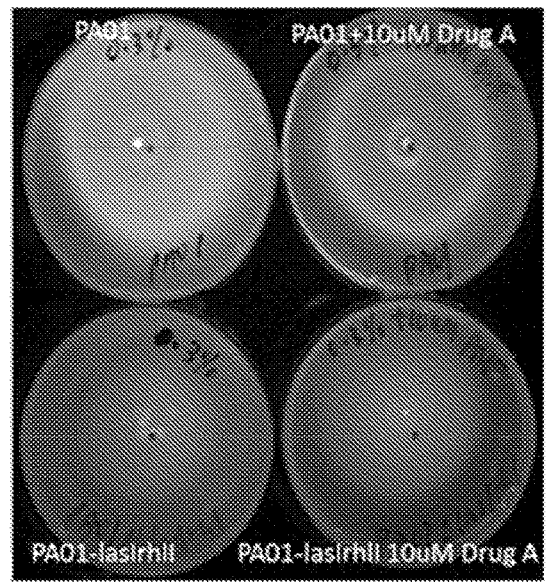
FIG. 5C shows that auranofin (drug A) does not inhibit swimming motility in *P. aeruginosa* as it is independent of Type IV pili (top-left dish shows a control assay of PA01, top-right dish shows a PA01 assay with 10 μM drug A, bottom-left dish shows an assay of PA01-lasIrhlI and bottom-right dish shows an assay of PA01-lasIrhlI with 10 μM drug A).

Motility assays were also carried out to show that auranofin (drug A) was able to inhibit swarming and twitching motility in *P. aeruginosa* (FIGS. 5A and 5B), which requires Type IV pili function. The top-left and bottom-left petri dishes contain *P. aeruginosa* (PA01) and PA01-lasIrhlI, respectively, serving as the controls. The top-right petri dish contains PA01 assay with 10 µM drug A while the bottom-right dish shows an assay of PA01-lasIrhlI with 10 µM drug A.

Figure 6:
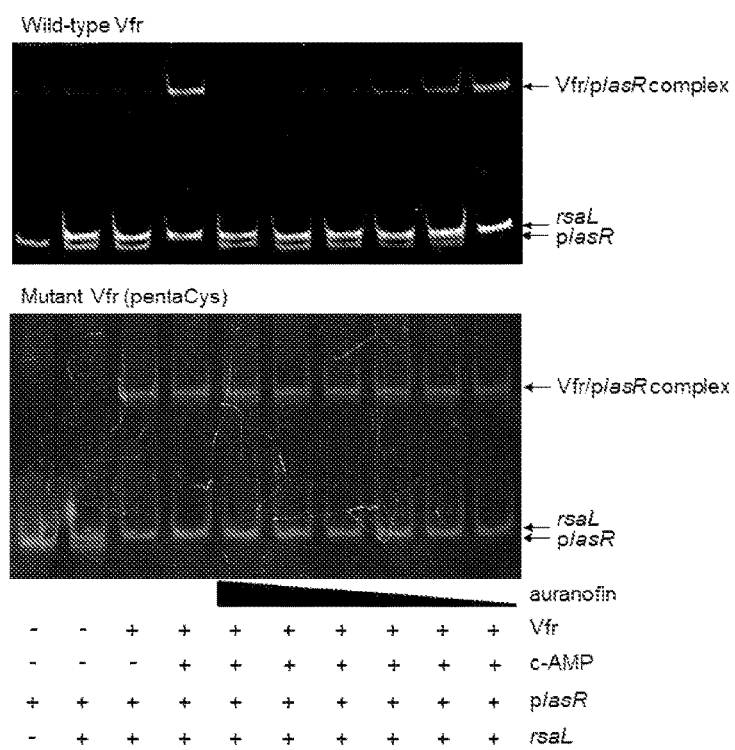
FIG. 6 shows electrophoretic mobility shift assays (EMSA) that indicate the effects of auranofin treatment at increasing concentrations on the binding of wild-type and mutant Vfr (pentaCys) to DNA fragments containing the promoter of lasR (plasR). It depicts auranofin inhibiting the binding of wild-type Vfr, but not of the mutant pentaCys variant, to a DNA fragment containing the lasR promoter sequence (plasR) in a dose dependent manner.
Figure 7A:
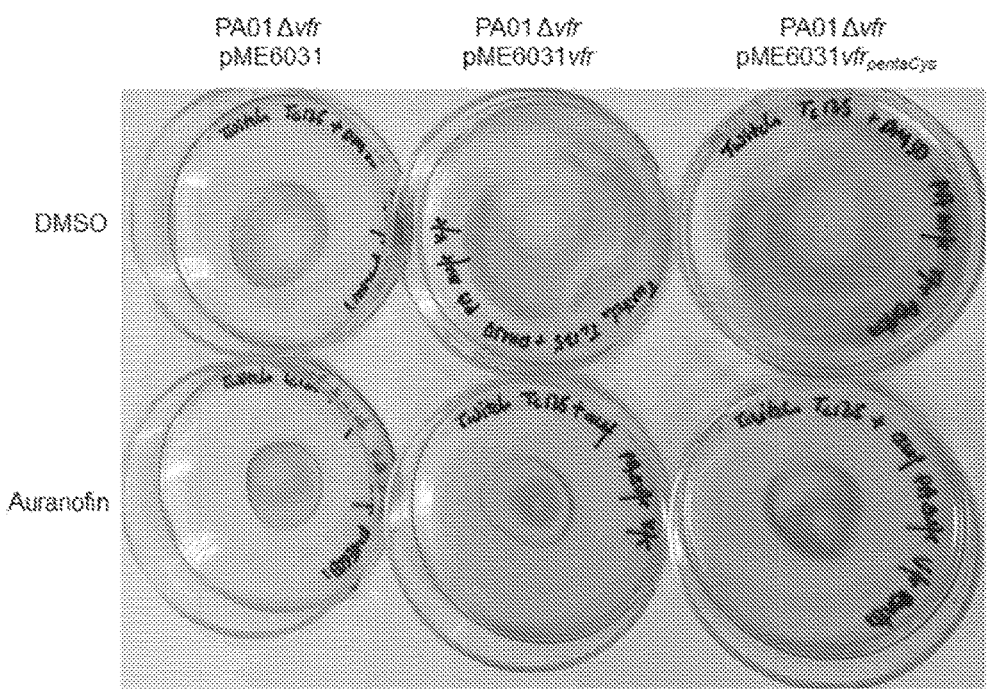
FIG. 7A shows auranofin still inhibits twitching motility in Δvfr strains complemented with the pentaCys variant of Vfr, indicating that there are other targets in these pathways.
Figure 7B:
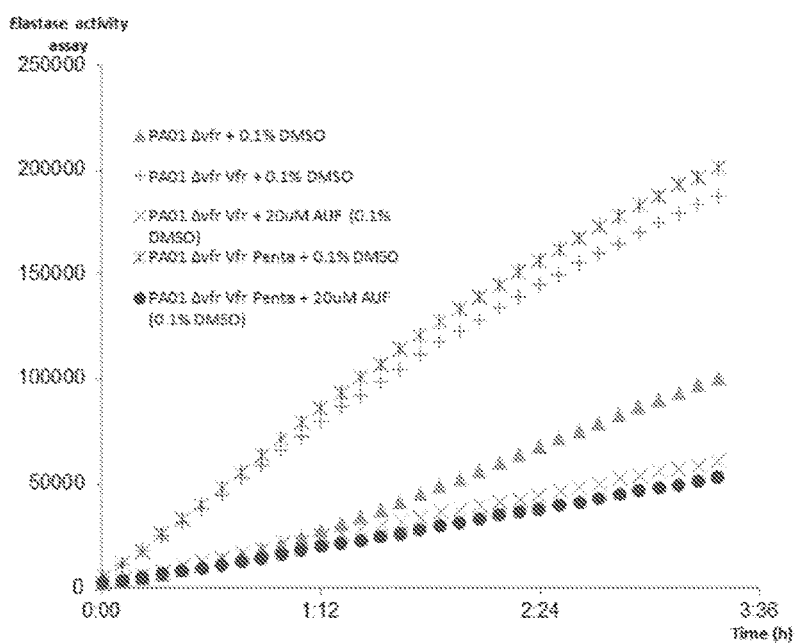
FIG. 7B shows auranofin still inhibits quorum sensing (as judged by LasB production) in Δvfr strains complemented with the pentaCys variant of Vfr, indicating that there are other targets in these pathways.

Example 3: Inhibition of Vfr by Auranofin Based on Electrophoretic Mobility Shift Assays It was hypothesized that auranofin inhibits Vfr, a global response regulator dependent on cyclic-AMP, which is known to control Type III secretion, Type IV pilus assembly and the quorum sensing networks (las and rhl). This was validated using electrophoretic mobility shift assays (EMSA) (see FIG. 6). Based on the EMSA, it can be seen that the binding of wild-type Vfr to the promoter of lasR (plasR), was inhibited by treatment with auranofin. In contrast, the binding of mutant Vfr proteins (C38S/C97S or C38S/C183S) to the same DNA fragment was not inhibited by auranofin. These results demonstrated that auranofin is capable of inhibiting Vfr in vitro, which may in turn result in the down-regulation of quorum sensing (via lasR) and the Type III, IV systems. The inventors further showed that expressing wild-type Vfr or pentaCys Vfr complements a Δvfr strain in twitching and QS (FIGS. 7A and 7B). Auranofin was still able to inhibit twitching and QS in the strain expressing the pentaCys Vfr, however, indicating that there are other auranofin targets in these pathways.

Example 4: Biofilm Treatment with Auranofin

Figure 8:
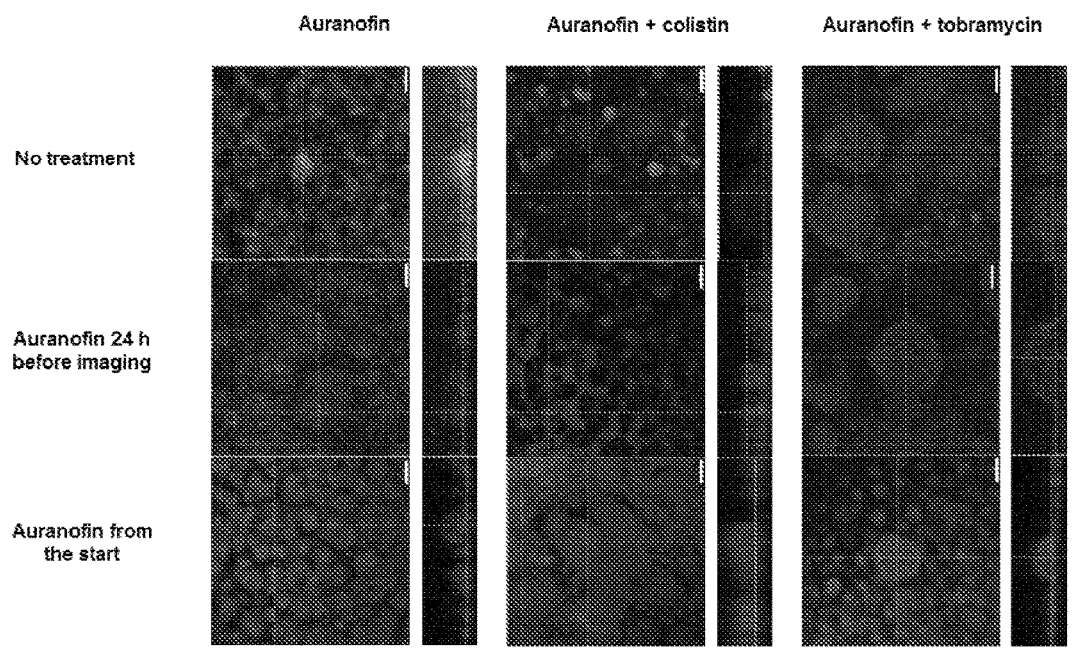
FIG. 8 depicts the effects of auranofin, and its combination either with colistin or tobramycin, on the morphology of biofilms formed using *P. aeruginosa* cells expressing green fluorescent protein (GFP). DNA from dead cells were labeled with propidium iodide. Auranofin was added either prior to (lower panels) or after formation of the biofilm (24 h before imaging, middle panels). Colistin and tobramycin were added after formation of the biofilm (24 h before imaging, middle panels). As shown in the figure, auranofin affects biofilm morphology and exhibits synergistic effects with colistin and tobramycin in biofilm eradication. Scale bar: 5 μm.

Quorum sensing inhibitors are known to affect biofilm morphology and structure. Since auranofin inhibits Vfr, which in turn affects quorum sensing, the effects of auranofin treatment on *P. aeruginosa* biofilms were investigated. As shown in FIG. 8, auranofin treatment prior to biofilm formation resulted in substantial cell death and the loss of the characteristic morphology of normal biofilms. It was also observed that treatment of auranofin together with the use of either one of two antibiotics (colistin or tobramycin) produces synergistic effects in biofilm morphology disruption and killing.

Based on the above examples, potential applications of various embodiments of the present invention may include re-purposing of auranofins and the development of new gold(I)-containing and/or auranofin-based analogs for the treatment of *P. aeruginosa* biofilm infections in, for example, in cystic fibrosis and chronic wound patients.

While the present invention has been particularly shown and described with reference to exemplary embodiments thereof, it will be understood by those of ordinary skill in the art that various changes in form and details may be made therein without departing from the spirit and scope of the present invention as defined by the following claims.

The invention claimed is:

1. A method of inhibiting quorum sensing in *Pseudomonas aeruginosa*, the method comprising contacting *Pseudomonas aeruginosa* with a gold(I) thiolate complex in an amount effective to inhibit quorum sensing in the *Pseudomonas aeruginosa*.

2. The method according to claim 1, wherein the gold(I) thiolate complex has Formula (I)

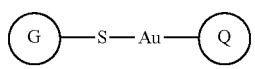     (I)

wherein

G is selected from the group consisting of a substituted or unsubstituted $C_1$-$C_{20}$ alkyl, a substituted or unsubstituted $C_1$-$C_{20}$ alkoxy, a substituted or unsubstituted $C_2$-$C_{20}$ alkenyl, a substituted or unsubstituted $C_2$-$C_{20}$ alkynyl, a substituted or unsubstituted $C_3$-$C_{20}$ alicyclic group, a substituted or unsubstituted $C_5$-$C_{15}$ aryl, a substituted or unsubstituted $C_6$-$C_{30}$ alkyl-aryl, a substituted or unsubstituted $C_3$-$C_{20}$ heterocycle, a substituted or unsubstituted $C_4$-$C_{30}$ alkyl-heterocycle and a substituted or unsubstituted $C_5$-$C_{15}$ heteroaryl, and Q is nothing, halogen, or $PR_3$, wherein each R is independently selected from the group consisting of H, halogen, a substituted or unsubstituted $C_1$-$C_{20}$ alkyl, a substituted or unsubstituted $C_1$-$C_{20}$ alkoxy, a substituted or unsubstituted $C_2$-$C_{20}$ alkenyl, a substituted or unsubstituted $C_2$-$C_{20}$ alkynyl, a substituted or unsubstituted $C_5$-$C_{15}$ aryl, and salts thereof.

3. The method according to claim 2, wherein G is a substituted or unsubstituted $C_1$-$C_{20}$ alkyl, a substituted or unsubstituted $C_3$-$C_{20}$ heterocycle, or a substituted or unsubstituted $C_4$-$C_{30}$ alkyl-heterocycle.

4. The method according to claim 2, wherein G is $C(R^a)(R^b)(R^c)$,     (i)

wherein $R^a$, $R^b$, and $R^c$ are independently selected from the group consisting of H, a substituted or unsubstituted $C_1$-$C_{20}$ alkyl, and salts thereof; or

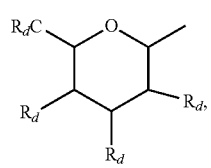     (ii)

wherein each $R^d$ is independently —OOR' or —OH, wherein R' is a substituted or unsubstituted $C_1$-$C_{20}$ alkyl.

5. The method according to claim 2, wherein G is selected from the group consisting of —CH(COO⁻Na⁺)(CH₂COOH),

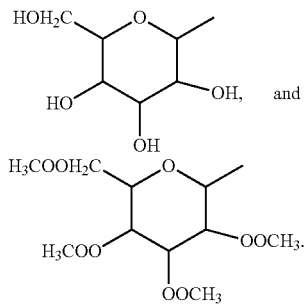

6. The method according to claim 2, wherein Q is nothing, —Cl, or —P(R^e)_3, wherein each $R^e$ is independently a substituted or unsubstituted $C_1$-$C_{20}$ alkyl.

7. The method according to claim 2, wherein Q is nothing or —P(CH₂CH₃)₃.

8. The method according to claim 1, wherein the gold(I) thiolate complex is selected from the group consisting of

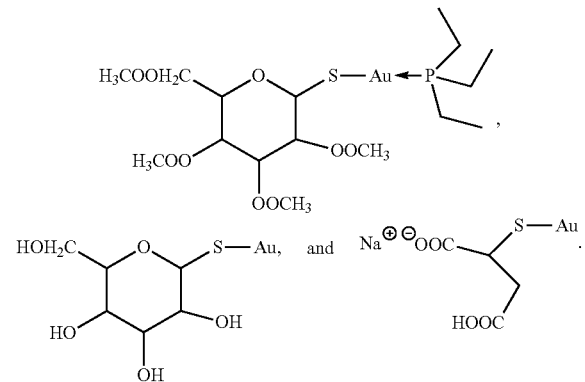

9. The method according to claim 1, wherein inhibiting the quorum sensing in the *Pseudomonas aeruginosa* comprises inhibiting a cyclic-AMP-dependent transcription regulator Vfr.

10. The method according to claim 1, wherein the *Pseudomonas aeruginosa* is contacted with the gold(I) thiolate complex ex vivo.

11. The method according to claim 10, wherein contacting the *Pseudomonas aeruginosa* with the gold(I) thiolate complex comprises administering the gold(I) thiolate complex to a surface.

12. The method according to claim 11, wherein the gold(I) thiolate complex is administered to the surface in an amount effective to inhibit biofilm formation associated with quorum sensing of the *Pseudomonas aeruginosa* on a medical device.

13. The method according to claim 1, wherein the *Pseudomonas aeruginosa* is contacted with the gold(I) thiolate complex in vivo.

14. The method according to claim 13, wherein the contacting comprises administering the gold(I) thiolate complex to a subject.

15. The method according to claim 14, wherein the subject is a mammalian subject.

16. The method according to claim 14, wherein the subject is afflicted with a disorder associated with quorum sensing, biofilm formation, or both and the gold(I) thiolate complex is administered in an amount effective to treat the disorder.

17. The method according to claim 1, wherein the gold(I) thiolate complex is present in a composition comprising an antibiotic.

18. The method according to claim 17, wherein the antibiotic is at least one of colistin or tobramycin.

19. A method for the treatment or prevention of damage or disease associated with quorum sensing, biofilm formation, or both in a subject, the method comprising: contacting *Pseudomonas aeruginosa* with a gold(I) thiolate complex in an amount effective to inhibit quorum sensing in the *Pseudomonas aeruginosa* by administering the gold(I) thiolate complex to a subject.

20. A method for the treatment of biofilm and/or for inhibiting biofilm formation of a component comprising a medical device, a personal hygiene article, a toiletry, a cosmetic, a disinfectant, a cleaning solution in a water treatment, or in a distribution system, the method comprising inhibiting quorum sensing in *Pseudomonas aeruginosa*, comprising contacting *Pseudomonas aeruginosa* with a gold (I) thiolate complex in an amount effective to inhibit quorum sensing in the *Pseudomonas aeruginosa* by contacting the component with the gold(I) thiolate complex.

* * * * *

UNITED STATES PATENT AND TRADEMARK OFFICE
CERTIFICATE OF CORRECTION

PATENT NO. : 10,258,640 B2
APPLICATION NO. : 15/758666
DATED : April 16, 2019
INVENTOR(S) : Michael Christian Givskov Page 1 of 1

It is certified that error appears in the above-identified patent and that said Letters Patent is hereby corrected as shown below:

In the Claims

Column 15, Line 35, Claim 2:
"Q is nothing, halogen, or $PR_3$" should read, --Q is nothing, halogen, or $-PR_3$--.

Column 15, Line 47, Claim 4:
"$C(R^a)(R^b)(R^c)$" should read, -- $-C(R^a)(R^b)(R^c)$--.

Signed and Sealed this
First Day of September, 2020

Andrei Iancu
*Director of the United States Patent and Trademark Office*